United States Patent
Oishi

(10) Patent No.: US 10,363,003 B2
(45) Date of Patent: Jul. 30, 2019

(54) X-RAY COMPUTED TOMOGRAPHY IMAGING APPARATUS AND DISPLAY APPARATUS

(71) Applicant: Toshiba Medical Systems Corporation, Otawara-shi (JP)

(72) Inventor: Keisuke Oishi, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 281 days.

(21) Appl. No.: 15/340,501

(22) Filed: Nov. 1, 2016

(65) Prior Publication Data

US 2017/0119323 A1    May 4, 2017

(30) Foreign Application Priority Data

Nov. 2, 2015  (JP) .................................. 2015-215602
Oct. 31, 2016  (JP) .................................. 2016-212508

(51) Int. Cl.
| A61B 6/04 | (2006.01) |
|---|---|
| A61B 6/03 | (2006.01) |
| A61B 6/08 | (2006.01) |
| A61B 6/10 | (2006.01) |
| A61B 6/00 | (2006.01) |

(52) U.S. Cl.
CPC .......... *A61B 6/0492* (2013.01); *A61B 6/032* (2013.01); *A61B 6/04* (2013.01); *A61B 6/0478* (2013.01); *A61B 6/08* (2013.01); *A61B 6/102* (2013.01); *A61B 6/464* (2013.01); *A61B 6/5205* (2013.01)

(58) Field of Classification Search
None
See application file for complete search history.

(56) References Cited

U.S. PATENT DOCUMENTS

| 2008/0019474 A1* | 1/2008 | Nakanishi | A61B 6/032 378/9 |
|---|---|---|---|
| 2014/0139215 A1* | 5/2014 | Gregerson | A61B 6/04 324/309 |
| 2018/0228457 A1* | 8/2018 | Muller | A61B 6/463 |

FOREIGN PATENT DOCUMENTS

| JP | 2002-328440 | 11/2002 |
|---|---|---|
| JP | 2012-45294 | 3/2012 |
| JP | 2013-9819 | 1/2013 |

* cited by examiner

*Primary Examiner* — Hoon K Song
(74) *Attorney, Agent, or Firm* — Oblon, McClelland, Maier & Neustadt, L.L.P.

(57) ABSTRACT

According to one embodiment, an X-ray computed tomography imaging apparatus includes an X-ray source, an X-ray detector, a gantry, a column, and a display. The display configured to display, on the floor surface, a graphic corresponding to one of a range in which a field of view formed by the X-ray source and the X-ray detector is projected onto the floor surface from a vertical direction of the gantry and a range in which an outer edge of the bore is projected onto the floor surface from the vertical direction of the gantry.

16 Claims, 7 Drawing Sheets

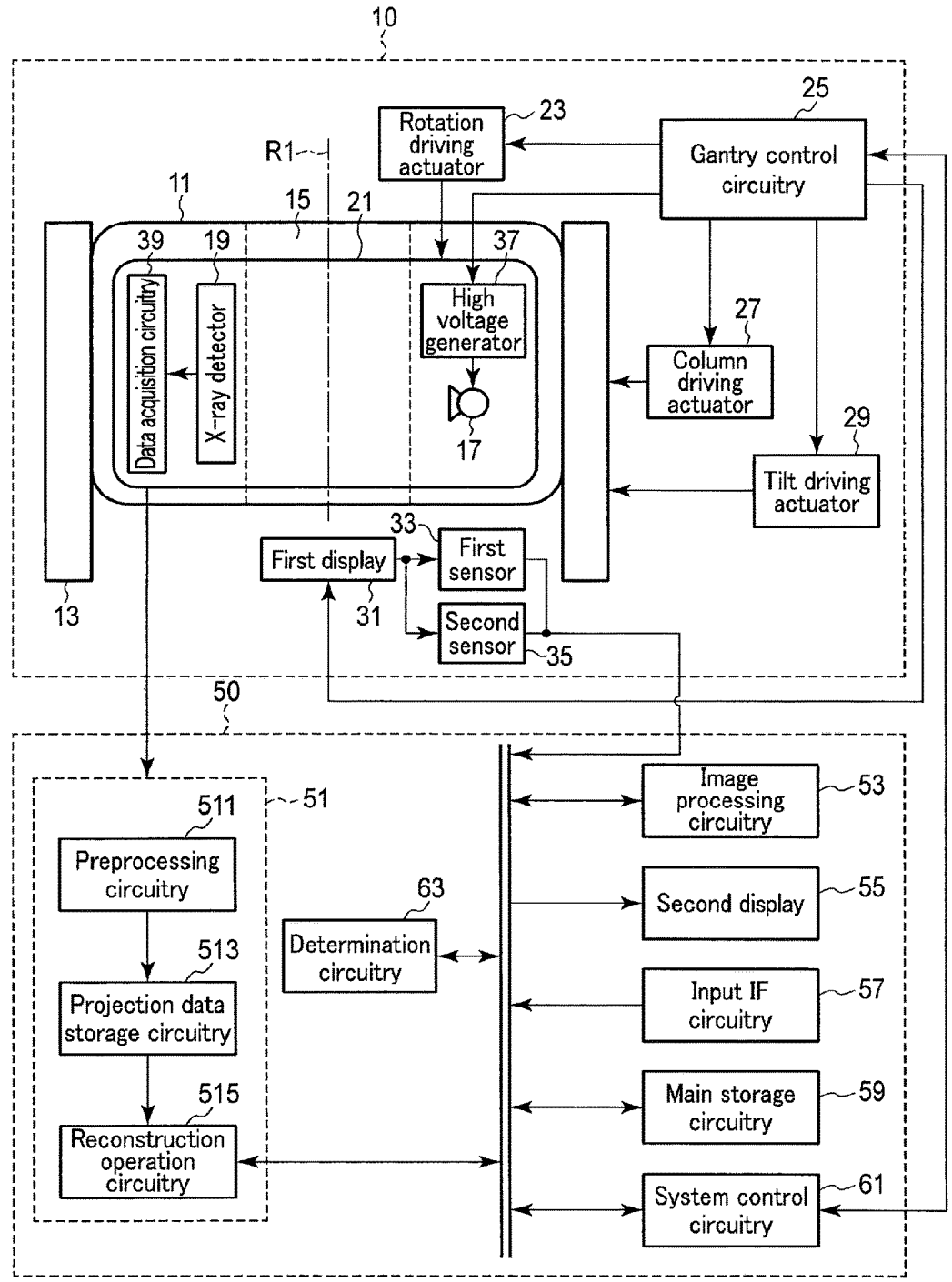
F I G. 1

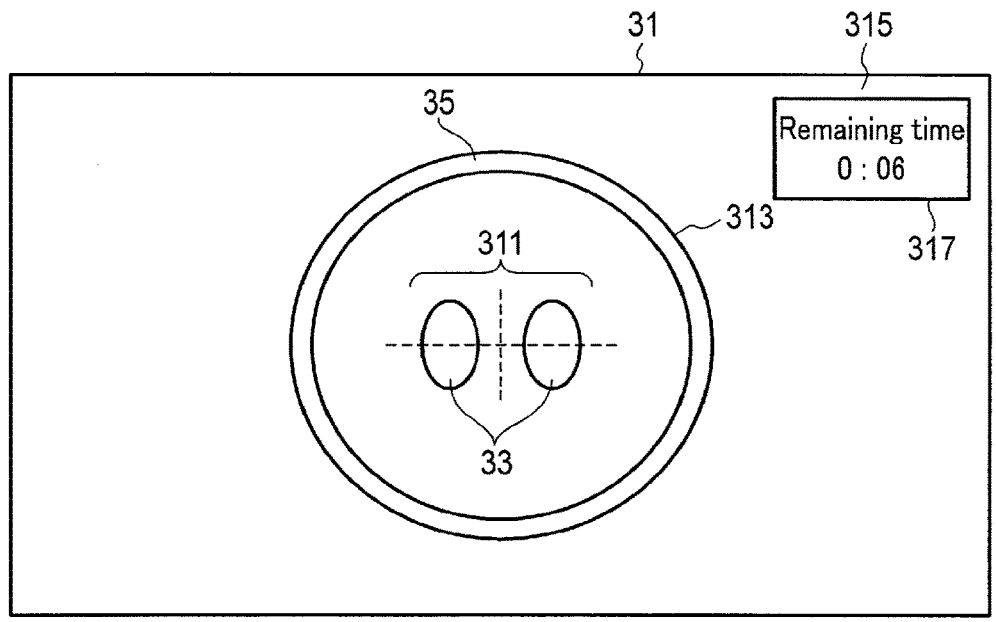
F I G. 2
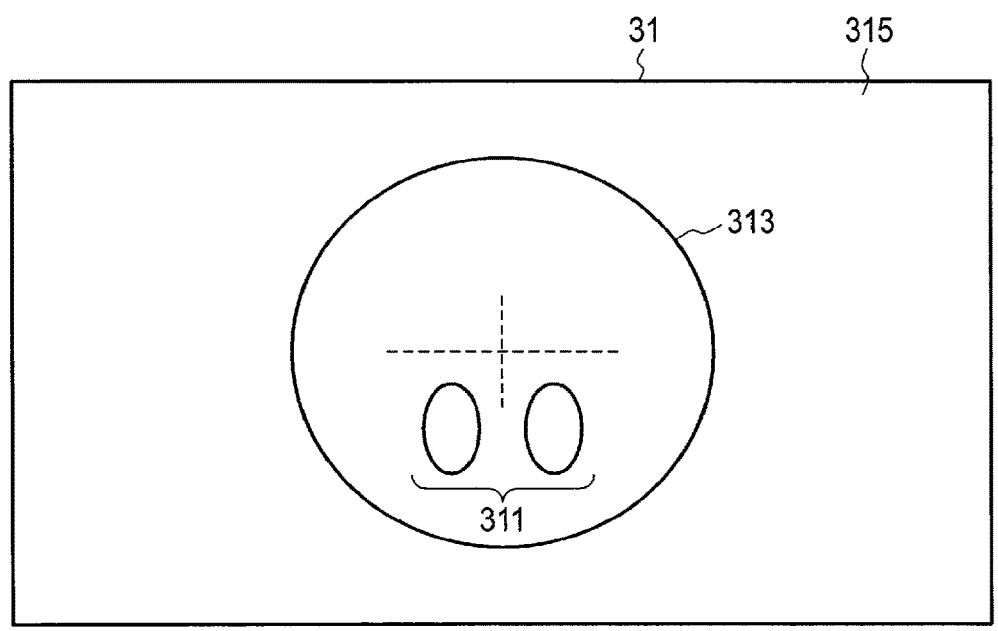
F I G. 3

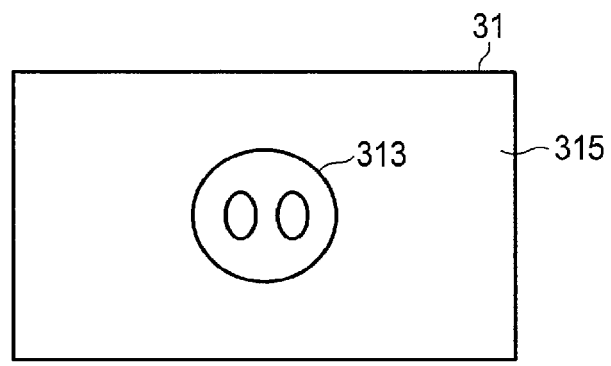
F I G. 4A
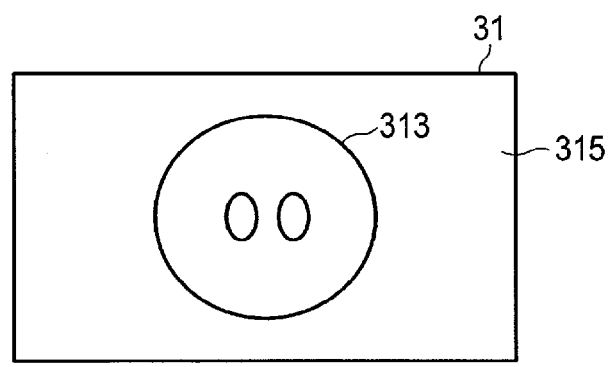
F I G. 4B
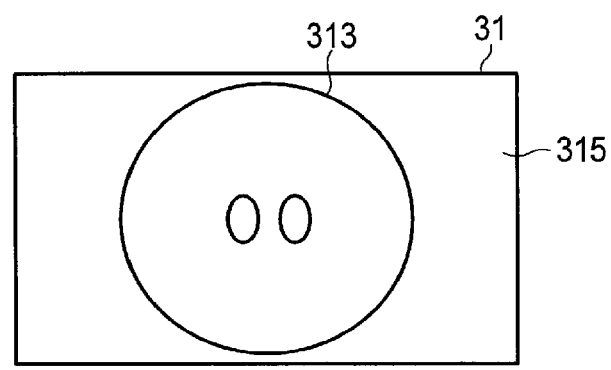
F I G. 4C

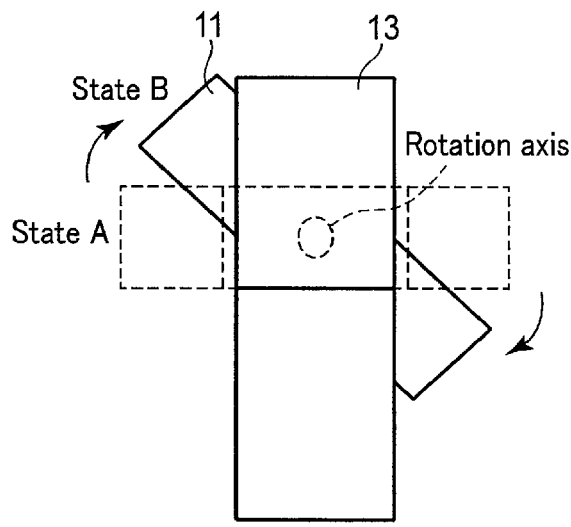
F I G. 5A
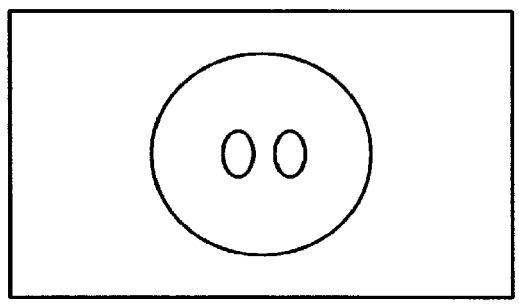
Display in state A
F I G. 5B
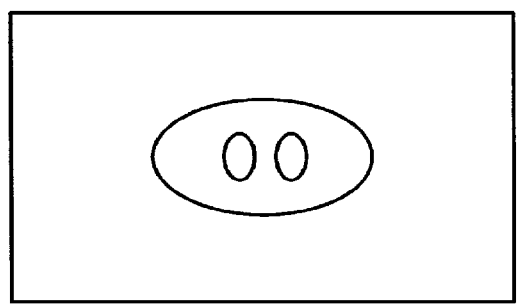
Display in state B
F I G. 5C

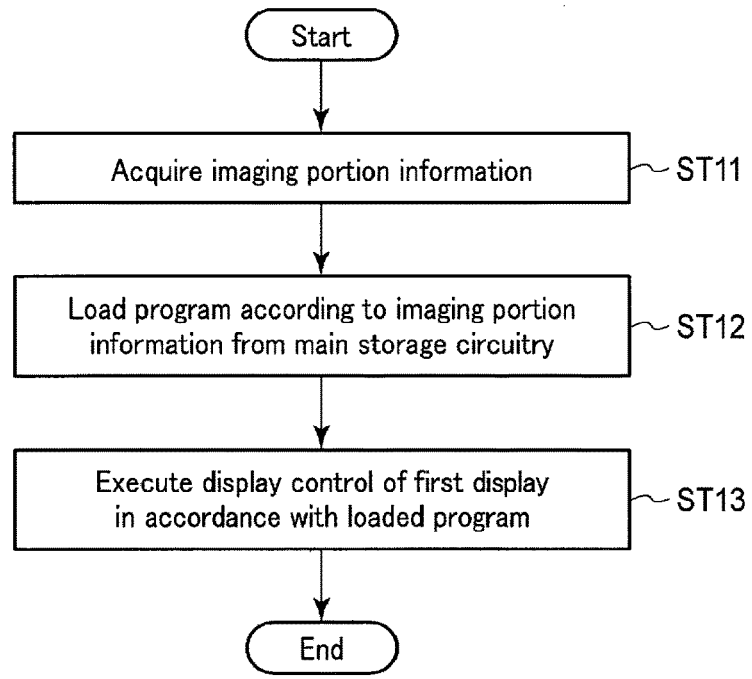
F I G. 6
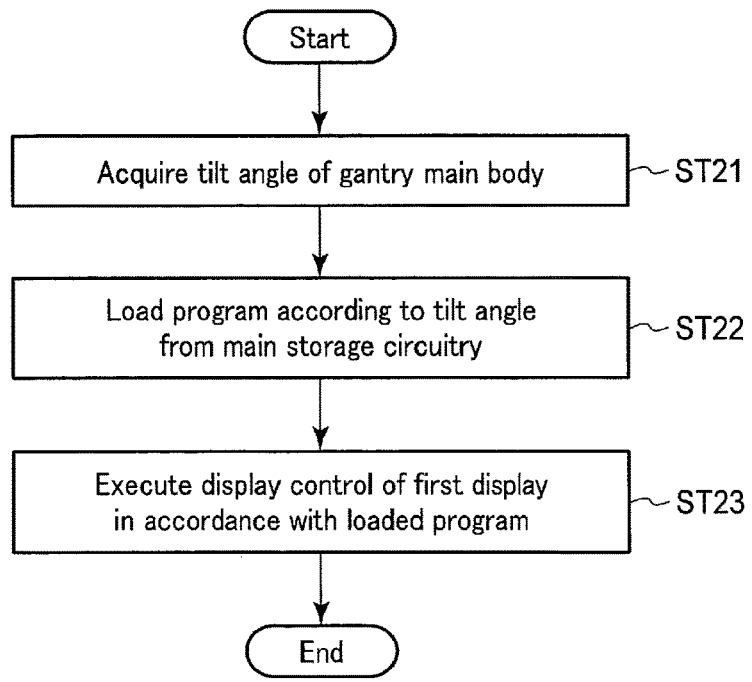
F I G. 7

X-RAY COMPUTED TOMOGRAPHY IMAGING APPARATUS AND DISPLAY APPARATUS

CROSS-REFERENCE TO RELATED APPLICATIONS

This application is based upon and claims the benefit of priority from Japanese Patent Application No. 2015-215602, filed Nov. 2, 2015, and No. 2016-212508, filed Oct. 31, 2016, the entire contents of which are incorporated herein by reference.

FIELD

Embodiments described herein relate generally to an X-ray computed tomography imaging apparatus and a display apparatus.

BACKGROUND

X-ray CT (Computed Tomography) imaging is normally performed in a lying state in which a patient lies on a bed. In recent years, CT imaging in a standing or sitting state is demanded in diagnosis of swallowing or the like.

When performing CT imaging in the standing or sitting state, it is necessary to make a patient stand at an appropriate position to prevent contact between the patient and the gantry. It is also necessary to determine whether the patient is standing at an appropriate position. However, a method of making a patient stand at an appropriate position and a method of determining whether the patient is standing at an appropriate position when performing CT imaging in the standing or sitting state are not established yet.

BRIEF DESCRIPTION OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing the arrangement of an X-ray computed tomography imaging apparatus according to the embodiment;

FIG. 2 is a view for explaining a first display shown in FIG. 1;

FIG. 3 is a view showing an example of display of a predetermined standing position on the first display shown in FIG. 1;

FIG. 4A is a view showing an example of display of a graphic whose size changes in correspondence with the imaging region on the first display shown in FIG. 1;

FIG. 4B is a view showing an example of display of a graphic whose size changes in correspondence with the imaging region on the first display shown in FIG. 1;

FIG. 4C is a view showing an example of display of a graphic whose size changes in correspondence with the imaging region on the first display shown in FIG. 1;

FIG. 5A is a view showing an example of display of an imaging region on the first display according to the tilt angle of a gantry;

FIG. 5B is a view showing an example of display of the imaging region on the first display according to the tilt angle of the gantry;

FIG. 5C is a view showing an example of display of the imaging region on the first display according to the tilt angle of the gantry;

FIG. 6 is a flowchart showing the procedure of display control of the first display according to an imaging portion in the X-ray computed tomography imaging apparatus according to the embodiment;

FIG. 7 is a flowchart showing the procedure of display control of the first display according to the tilt angle of the gantry in the X-ray computed tomography imaging apparatus according to the embodiment;

DETAILED DESCRIPTION

Figure 8:
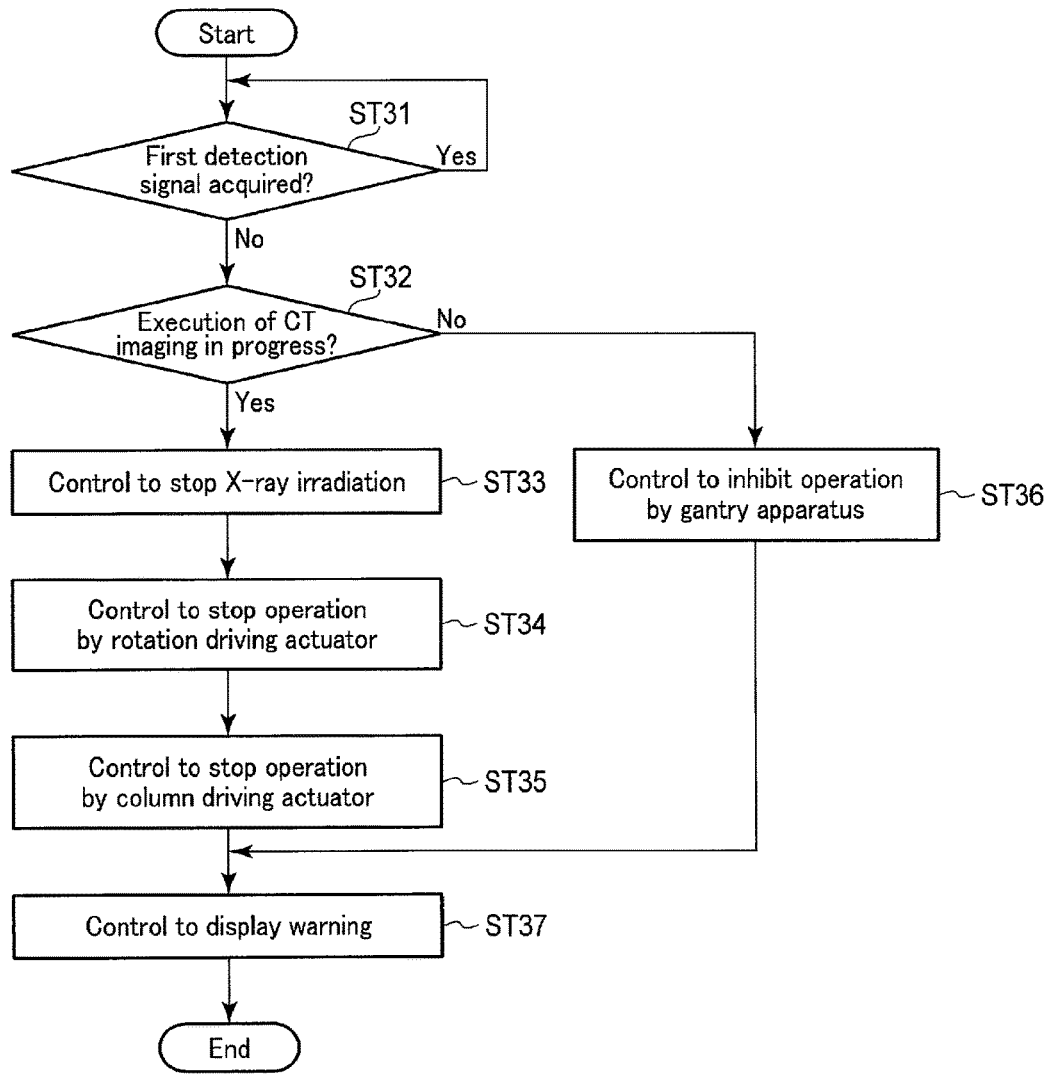
FIG. 8 is a flowchart showing the procedure of operation control in a case in which a subject is not located at a predetermined standing position in the X-ray computed tomography imaging apparatus according to the embodiment.

In general, according to one embodiment, an X-ray computed tomography imaging apparatus includes an X-ray source, an X-ray detector, a gantry, a column, and a display. The X-ray source configured to generate X-rays. The X-ray detector configured to detect the X-rays transmitted through a subject. The gantry configured to hold the X-ray source and the X-ray detector. The column configured to maintain a center axis of a bore of the gantry perpendicular to a floor surface and support the gantry movably in a vertical direction with respect to the floor surface. The display configured to display, on the floor surface, a graphic corresponding to one of a range in which a field of view formed by the X-ray source and the X-ray detector is projected onto the floor surface from the vertical direction of the gantry and a range in which an outer edge of the bore included the field of view is projected onto the floor surface from the vertical direction of the gantry.

An X-ray computed tomography imaging apparatus according to the embodiment will now be described with reference to the accompanying drawing. Note that the same reference numerals denote constituent elements having almost the same functions and arrangements in the following explanation, and a repetitive description thereof will be made only when necessary.

FIG. 1 is a block diagram showing an X-ray computed tomography imaging apparatus according to this embodiment.

As shown in FIG. 1, an X-ray computed tomography imaging apparatus (to be referred to as an X-ray CT apparatus hereinafter) according to this embodiment includes a gantry apparatus 10 and a console 50. For example, the gantry apparatus 10 is placed in a CT examination room, and the console 50 is placed in a control room adjacent to the CT examination room. The gantry apparatus 10 and the console 50 are connected wirelessly or via a cable to be communicable with each other. The gantry apparatus 10 is a scanning apparatus having an arrangement for performing X-ray computed tomography imaging (to be referred to as CT imaging hereinafter) of a subject in a standing, sitting, or lying position. The console 50 is a computer or workstation configured to control the gantry apparatus 10.

As shown in FIG. 1, a gantry 11 is an almost cylindrical structure with a bore 15 that forms an imaging region. The imaging region almost matches an FOV (Field Of View) in CT imaging in a standing, sitting, or lying state. The gantry 11 stores an X-ray tube 17 and an X-ray detector 19 which are arranged to face each other via the bore 15.

More specifically, the gantry 11 further includes a main frame made of a metal such as aluminum, and a rotation frame 21 supported by the main frame via a bearing and the like to be rotatable about a center axis R1. An annular electrode is provided on the contact portion of the main frame to the rotation frame 21. A conductive sliding element is attached to the contact portion of the main frame to be in slidable contact with the annular electrode. The rotation frame 21 is a metal frame formed into a ring shape by a metal such as aluminum, to which, for example, the X-ray tube 17 and the X-ray detector 19 are attached. The X-ray tube 17 and the X-ray detector 19 may be, for example, fitted in concave portions formed in the rotation frame 21 or fastened using fasteners such as a screw.

The rotation frame 21 rotates about the center axis R1 at a predetermined angular velocity upon receiving power from a rotation driving actuator 23. The rotation driving actuator 23 generates the power to rotate the rotation frame 21 under the control of gantry control circuitry 25. The rotation driving actuator 23 drives at a rotation speed corresponding to the duty ratio or the like of a driving signal from the gantry control circuitry 25, thereby generating the power. The rotation driving actuator 23 is implemented by, for example, a motor such as a direct drive motor or a servo motor. In this embodiment, the rotation driving actuator 23 is stored in, for example, the gantry 11.

A column 13 is a base that supports the gantry 11 away from the floor surface. The column 13 has, for example, a columnar shape such as a circular prismatic shape or a prismatic shape. The column 13 is made of, for example, an arbitrary substance such as a plastic or a metal. The column 13 is attached to, for example, a side surface of the gantry 11. To perform X-ray computed tomography imaging of the subject in the standing position, the columns 13 slidably support the gantry 11 in a state in which the center axis R1 of the bore 15 is kept perpendicular to the floor surface.

The column 13 stores a driving actuator (to be referred to as a column driving actuator hereinafter) 27 for sliding of the gantry 11 in the vertical direction. The column driving actuator 27 generates power to slide the gantry 11 in the vertical direction under the control of the gantry control circuitry 25. More specifically, the column driving actuator 27 drives at a rotation speed corresponding to the duty ratio or the like of a driving signal from the gantry control circuitry 25, thereby generating the power. The column 13 slides the gantry 11 in the vertical direction with respect to the column 13 upon receiving the power from the column driving actuator 27. The column driving actuator 27 is implemented by, for example, a motor such as a direct drive motor or a servo motor.

The column 13 supports, for example, the gantry 11 rotatably about the horizontal axis (also called a rotation axis and will be referred to as a tilt axis hereinafter) of the gantry 11. In this case, the column 13 and the gantry 11 are connected via a bearing 77 and the like such that the gantry 11 can rotate about the tilt axis.

The column 13 stores a driving actuator (to be referred to as a tilt driving actuator hereinafter) 29 for tilt of the gantry 11 about the tilt axis. The tilt driving actuator 29 generates power to rotate the gantry 11 about the tilt axis under the control of the gantry control circuitry 25. More specifically, the tilt driving actuator 29 drives at a rotation speed corresponding to the duty ratio or the like of a driving signal from the gantry control circuitry 25, thereby generating the power.

The column 13 tilts the gantry 11 about the tilt axis upon receiving the power from the tilt driving actuator 29. The tilt driving actuator 29 is implemented by, for example, a motor such as a direct drive motor or a servo motor.

This allows the single gantry apparatus 10 to selectively execute standing or sitting position imaging and lying position imaging.

The columns 13 are provided on both sides of the gantry 11. However, the embodiment is not limited to this. For example, one column 13 may be connected to only one of the both sides of the gantry 11. The column 13 has a columnar shape. However, the embodiment is not limited to this. For example, the column 13 may have any shape such as a U shape as long as it can support at least one side portion of the gantry 11.

A first display 31 displays, on the floor surface, a graphic corresponding to projection of the imaging region or the outer edge of the bore 15 to the floor surface. The outer edge of the bore 15 corresponds to the inner edge of the gantry 11. In CT imaging by the gantry 11, the first display 31 displays the graphic on the floor surface, thereby displaying a predetermined standing or sitting position of the subject. The imaging region almost matches the field of view (FOV) in CT imaging in a standing, sitting, or lying state.

The first display 31 is placed on the floor surface located under the gantry 11. The first display 31 may be, for example, a mat (floor covering mat) placed on the floor surface of the examination room every time an examination is conducted. In this case, a marker or the like may be placed on the floor surface of the examination room so that the mat can be placed at a correct position after detachment. The first display 31 may be, for example, an electric notice board using a liquid crystal display and LEDs, which may permanently be embedded in the floor of the examination room.

FIG. 2 is a view for explaining the first display 31 shown in FIG. 1.

As shown in FIG. 2, the first display 31 displays a predetermined standing position 311 of the subject in an imaging region 313. In this embodiment, the first display 31 displays a graphic corresponding to a range in which a field of view formed by the X-ray tube 17 and the X-ray detector 19 is projected onto the floor surface from the vertical direction of the gantry 11 or a range in which the outer edge of the bore 15 is projected onto the floor surface from the vertical direction of the gantry 11. Referring to FIG. 2, the first display 31 displays the predetermined standing position 311 of the subject, for example, at the center of the imaging region 313. The center of the imaging region 313 almost matches the center of the bore 15. Note that FIG. 2 illustrates the standing position 311 of the subject as an example. However, the embodiment is not limited to this. The first display 31 may display the sitting position of the subject or the placement position of a chair or the like used to set the subject in the sitting state. Note that the display concerning the predetermined standing position 311 of the subject may be implemented by, for example, display control of the first display 31 by system control circuitry 61 according to a program stored in main storage circuitry 59.

A first sensor 33 is provided at the standing position 311. The first sensor 33 is, for example, a touch sensor capable of detecting contact of the subject, a piezoelectric sensor capable of detecting a weak current generated by a pressure, or a load sensor capable of detecting the load of the subject. Upon detecting the subject, the first sensor 33 transmits the subject detection signal (to be referred to as a first detection signal hereinafter) to determination circuitry 63 in the console 50. When a load sensor is used as the first sensor 33, a load can be detected. Hence, the center of gravity of the subject can be grasped. That is, the tilt of the subject can be grasped. Note that in FIG. 2, the first sensor 33 is placed at the standing position 311. However, the embodiment is not limited to this. The first sensor 33 may be placed all over the imaging region 313.

A second sensor 35 is placed along the outline of the imaging region 313. The second sensor 35 is, for example, an optical sensor using a laser beam or the like. For example, when the subject blocks an emitted laser beam, the second sensor 35 transmits a subject detection signal (to be referred to as a second detection signal hereinafter) to the determination circuitry 63 in the console 50. Note that a light source such as an LED may be placed in place of the second sensor 35. This can visually notify the subject and the operator that the subject is located outside the imaging region 313. The second sensor 35 is provided along the outline of the imaging region 313. However, the embodiment is not limited to this. The second sensor 35 may be placed all over the imaging region 313.

In addition, for example, additional information 317 to be added to the subject in CT imaging is displayed in a region 315 outside the imaging region 313 of the first display 31. More specifically, there is displayed the additional information 317 such as a breath holding time in chest CT imaging for mainly capturing the lungs and heart, abdominal CT imaging for mainly capturing the stomach and intestines, or the like, or a warning to notify the subject that, for example, the subject is not located at the predetermined standing or sitting position or is located outside the imaging region 313. In addition, the additional information 317 representing the posture (for example, a static posture such as standing or sitting) of the subject in CT imaging is displayed. Note that to facilitate visual recognition of the additional information 317, the additional information 317 is displayed on the front side of the subject. In FIG. 2, the breath holding time is displayed on the front side of the subject as an example of the additional information 317. These pieces of additional information can be changed and added any time in accordance with a predetermined scanning plan or imaging method. A method of displaying the additional information 317 is not limited to that shown in FIG. 2.

The first display 31 may change the display concerning the standing position 311 in accordance with examination information about CT imaging. The examination information includes, for example, patient information such as a patient name, sex, height, and weight and imaging portion information of CT imaging. More specifically, the first display 31 may change the display concerning the predetermined standing position 311 of the subject in the imaging region 313 in accordance with the imaging portion of the subject. FIG. 3 is a view showing an example of display of the predetermined standing position 311 on the first display 31 shown in FIG. 1. For example, as shown in FIG. 3, the predetermined standing position 311 of the subject may be displayed at a position shifted from the center of the imaging region 313. The display concerning the predetermined standing position 311 of the subject may be implemented by, for example, display control of the first display 31 by the system control circuitry 61 according to a program stored in the main storage circuitry 59.

The first display 31 may select a graphic from a plurality of graphics stored in the main storage circuitry 59 in advance and display the selected graphic. FIGS. 4A to 4C are views showing examples of display of a graphic whose size changes in correspondence with the imaging region 313 on the first display 31 shown in FIG. 1. For example, as shown in FIGS. 4A to 4C, the first display 31 may select a graphic of S, M, or L size in accordance with the imaging portion and display the selected graphic as the imaging region 313. Alternatively, an input button may be provided on the first display 31, and the graphic may be changed by pressing the input button.

The first display 31 may change the graphic to be displayed in accordance with the rotation angle (to be referred to as a tilt angle hereinafter) of the gantry 11 about the tilt axis. FIGS. 5A to 5C are views showing examples of display of the imaging region 313 on the first display 31 according to the tilt angle of the gantry 11. If the gantry 11 is in a state A, as shown in FIG. 5A, the first display 31 displays the imaging region 313 as a perfect circle, as shown in FIG. 5B. On the other hand, if the gantry 11 is in a state B, as shown in FIG. 5A, the first display 31 displays the imaging region 313 as an ellipse, as shown in FIG. 5C.

The displayed graphic is changed to make it almost match the projection of the imaging region 313 onto the floor surface in accordance with the tilt angle. In other words, this is because the imaging region 313 looks elliptic when the gantry 11 is viewed from the upper side. The display of the graphic according to the tilt angle may be implemented by selecting a graphic according to the tilt angle of the gantry 11 about the tilt axis from a plurality of graphics stored in the main storage circuitry 59 in advance and performing display control of the first display 31 in accordance with the selected graphic. Alternatively, the display of the graphic according to the tilt angle may be implemented by reading out a program according to the tilt angle from programs stored in the main storage circuitry 59 and performing display control of the first display 31 in accordance with the readout program. At this time, the system control circuitry 61 may, for example, calculate an elliptic from the tilt angle.

The X-ray tube 17 generates X-rays upon receiving a high voltage applied from a high voltage generator 37. The high voltage generator 37 is attached to, for example, the rotation frame 21. Under the control of the gantry control circuitry 25, the high voltage generator 37 generates a high voltage to be applied to the X-ray tube 17 from power supplied from the power supply unit of the gantry 11 via the annular electrode. The high voltage generator 37 and the X-ray tube 17 are connected via a high voltage cable. The high voltage generated by the high voltage generator 37 is applied to the X-ray tube 17 via the high voltage cable.

The X-ray detector 19 detects the X-rays generated by the X-ray tube 17 and transmitted through a subject. The X-ray detector 19 includes a plurality of X-ray detection elements arranged on a two-dimensional curved surface. Each X-ray detection element detects the X-rays from the X-ray tube 17 and converts them into an electrical signal having a peak value according to the intensity of the detected X-rays. Each X-ray detection element includes, for example, a scintillator and a photoelectric converter. The scintillator generates fluorescence upon receiving X-rays. The photoelectric converter converts the generated fluorescence into a charge pulse. The charge pulse has a peak value according to the intensity of the X-rays. More specifically, a device such as a photomultiplier or a photodiode, which converts photons into an electrical signal, is used as the photoelectric converter. Note that the X-ray detector 19 according to this embodiment is not limited to a detector of an indirect type that temporarily converts X-rays into fluorescence and then converts it into an electrical signal, and may be a detector of a direct type that directly converts X-rays into an electrical signal.

Data acquisition circuitry 39 acquires, for each view, digital data representing the intensity of the X-rays attenuated by the subject. The data acquisition circuitry 39 is implemented by, for example, semiconductor integrated circuitry on which integration circuitry and an A/D converter provided in correspondence with each of the plurality of X-ray detection elements are implemented in parallel. The data acquisition circuitry 39 is connected to the X-ray detector 19 in the gantry 11. The integration circuitry integrates electrical signals from an X-ray detection element during a predetermined view period to generate an integrated signal. The A/D converter A/D-converts the generated integrated signal to generate digital data having a data value corresponding to the peak value of the integrated signal. The digital data after conversion is called raw data. Raw data is a set of digital values of X-ray intensity identified by the channel number and the column number of an X-ray detection element as the generation source and a view number representing an acquired view. The raw data is supplied to the console 50 via, for example, a noncontact data transmission unit stored in the gantry 11.

Note that the gantry 11 may store not only the X-ray tube 17, the X-ray detector 19, the rotation frame 21, the main frame, the power supply apparatus, the high voltage generator 37, and the data acquisition circuitry 39 described above but also various other units necessary for Ct imaging. For example, a cooling apparatus cools the X-ray tube may be attached to the rotation frame 21. A fan for air conditioning may be attached to the gantry 11.

The gantry control circuitry 25 controls the high voltage generator 37, the rotation driving actuator 23, the column driving actuator 27, and the tilt driving actuator 29 under the control of system control circuitry 61 in the console 50. The gantry control circuitry 25 includes, as hardware resources, a processing unit (processor) such as a CPU or an MPU and a storage unit (memory) such as a ROM or a RAM. The gantry control circuitry 25 may be implemented by an ASIC, an FPGA, a CPLD, an SPLD, or the like. The processing unit implements the function by reading out a program saved in the storage unit and executing it. Note that instead of saving the program in the storage unit, the program may directly be installed in circuitry of the processing unit. In this case, the processing unit implements the function by reading out the program installed in the circuitry and executing it.

The console 50 includes image reconstruction circuitry 51, image processing circuitry 53, a second display 55, input interface (IF) circuitry 57, main storage circuitry 59, and the system control circuitry 61 which are connected via a bus. Data communication between the image reconstruction unit 51, the image processing circuitry 53, the second display 55, the input IF circuitry 57, the main storage circuitry 59, and the system control circuitry 61 is performed via the bus.

The image reconstruction circuitry 51 reconstructs a CT image concerning the subject based on raw data from the console 50. More specifically, the image reconstruction unit 51 includes preprocessing circuitry 511, projection data storage circuitry 513, and reconstruction operation circuitry 515. The preprocessing circuitry 511 preprocesses raw data from the gantry apparatus 10. The preprocessing includes logarithmic transformation and various kinds of correction processing such as X-ray intensity correction and offset correction. The preprocessed raw data is called projection data. The projection data storage circuitry 513 is a storage unit that stores the projection data generated by the preprocessing circuitry 511, such as an HDD, an SSD, or an integrated circuitry storage unit. The reconstruction operation circuitry 515 generates a CT image that expresses the spatial distribution of CT values concerning the subject based on the projection data. As the image reconstruction algorithm, an existing image reconstruction algorithm, for example, an analytic image reconstruction method such as FBP (Filtered Back Projection) or CBP (Convolution Back Projection) or a statistical image reconstruction method such as ML-EM (Maximum Likelihood Expectation Maximization) or OS-EM (Ordered Subset Expectation Maximization) is used.

The image reconstruction circuitry 51 includes, as hardware resources, a processing unit (processor) such as a CPU, an MPU, or a GPU (Graphics Processing Unit) and a storage unit (memory) such as a ROM or a RAM. The image reconstruction unit 51 may be implemented by an ASIC, an FPGA, a CPLD, an SPLD, or the like. The processing unit implements the functions of the preprocessing circuitry 511 and the reconstruction operation circuitry 515 by reading out a program saved in the storage unit and executing it. Note that instead of saving the program in the storage unit, the program may directly be installed in circuitry of the processing unit. In this case, the processing unit implements the functions of the preprocessing circuitry 511 and the reconstruction operation circuitry 515 by reading out the program installed in the circuitry and executing it. Alternatively, dedicated hardware circuitry functioning as the preprocessing circuitry 511 and dedicated hardware circuitry functioning as the reconstruction operation circuitry 515 may be implemented in the image reconstruction circuitry 51.

The image processing circuitry 53 performs various kinds of image processing for the CT image reconstructed by the image reconstruction circuitry 51. For example, if the CT image is volume data, the image processing circuitry 53 performs three-dimensional image processing such as volume rendering, surface volume rendering, image value projection processing, MPR (Multi-Planer Reconstruction) processing, and CPR (Curved MPR) processing for the CT image to generate a display image. The image processing circuitry 53 includes, as hardware resources, a processing unit (processor) such as a CPU, an MPU, or a GPU and a storage unit (memory) such as a ROM or a RAM. The image processing unit 53 may be implemented by an ASIC, an FPGA, a CPLD, an SPLD, or the like.

The second display 55 displays various kinds of information such as a two-dimensional CT image and a display image. As the second display 55, for example, a CRT display, a liquid crystal display, an organic EL display, an LED display, a plasma display, or another arbitrary display known in the technical field can appropriately be used.

The input IF circuitry 57 accepts various kinds of instructions and information input from the user. As the input IF circuitry 57, a keyboard, a mouse, or various kinds of switches, or the like can be used. For example, an arbitrary tilt angle of the gantry 11 about the tilt axis is input to the input IF circuitry 57. Note that the input IF circuitry 57 may be provided on the console 50 or the gantry apparatus 10.

The main storage circuitry 59 is a storage unit that stores various kinds of information, such as an HDD, an SSD, or an integrated circuitry storage unit. The main storage circuitry 59 may be a driving actuator or the like reads/writes various kinds of information from/to a portable storage medium such as a CD-ROM drive, a DVD drive, or a flash memory. For example, the main storage circuitry 59 stores a control program and the like concerning CT imaging according to this embodiment. More specifically, the main storage circuitry 59 stores a program for executing display control according to an imaging portion. The main storage circuitry 59 also stores a plurality of graphics concerning the imaging region 313 in advance. For example, the main storage circuitry 59 stores the graphics of different sizes shown in FIGS. 4A to 4C. In addition, the main storage circuitry 59 stores a plurality of graphics corresponding to a plurality of rotation angles of the gantry 11 about the tilt axis.

The system control circuitry 61 includes the processing unit and the storage unit described above. The system control circuitry 61 functions as the core of the X-ray CT apparatus according to this embodiment. More specifically, the system control circuitry 61 reads out a control program stored in the main storage circuitry 59, loads it onto the memory, and controls the units of the X-ray CT apparatus in accordance with the loaded control program.

The determination circuitry 63 determines, based on, for example, the detection result of the first sensor 33, whether the subject is located at the predetermined standing position or sitting position. If the determination circuitry 63 determines that the subject is not located at the predetermined standing position or sitting position, the system control circuitry 61 controls to execute at least one of warning to notify the subject that the subject is not located at the predetermined standing or sitting position, inhibition of the sliding operation of the gantry 11, and stop of the sliding operation of the gantry 11 via the gantry control circuitry 25. The determination circuitry 63 also determines, based on, for example, the detection result of the second sensor 35, whether the subject is located outside the imaging region 313. If it is determined that the subject is located outside the imaging region 313, the system control circuitry 61 executes at least one of warning to notify the subject that the subject is located outside the imaging region 313, inhibition of the sliding operation of the gantry 11, and stop of the sliding operation of the gantry 11 via the gantry control circuitry 25.

Note that the image reconstruction circuitry 51, the image processing circuitry 53, the system control circuitry 61, and the determination circuitry 63 may be integrated on a single board in the console 50 or distributed to a plurality of boards.

An example of the operation of the X-ray CT apparatus according to this embodiment will be described here in detail with reference to the accompanying drawing.

(Display Control of the First Display 31 According to Imaging Portion)

FIG. 6 is a flowchart showing the procedure of display control of the first display 31 according to an imaging portion.

As shown in FIG. 6, the system control circuitry 61 acquires, for example, imaging portion information selected by the input IF circuitry 57 (step ST11). For example, an arbitrary imaging portion to execute CT imaging is selected, by the input IF circuitry 57, from a plurality of imaging portions displayed on the second display 55. The system control circuitry 61 reads out a program according to the acquired imaging portion information from the main storage circuitry 59 (step ST12). The system control circuitry 61 executes display control of the first display 31 in accordance with the readout program (step ST13). For example, the system control circuitry 61 controls the first display 31 to display the predetermined standing position 311 of the subject according to the selected imaging portion. The first display 31 thus displays the predetermined standing position 311 according to the selected imaging portion. In addition, the system control circuitry 61 controls the first display 31 to display a graphic of a size according to the selected imaging portion. An imaging region of a size according to the selected imaging portion is thus displayed.

Note that the system control circuitry 61 controls the first display 31 via the gantry control circuitry 25.

(Display Control of First Display 31 According to Tilt Angle of Gantry 11)

FIG. 7 is a flowchart showing the procedure of display control of the first display 31 according to the tilt angle of the gantry 11.

As shown in FIG. 7, the system control circuitry 61 acquires, for example, the tilt angle of the gantry 11 (step ST21). The tilt angle is input to, for example, the input IF circuitry 57 and transmitted. The system control circuitry 61 reads out a program according to the acquired tilt angle from the main storage circuitry 59 (step ST22). The system control circuitry 61 executes display control of the first display 31 in accordance with the readout program (step ST23). For example, the system control circuitry 61 controls the first display 31 to display a graphic according to the tilt angle. The imaging region 313 of a perfect circle or an ellipse according to the tilt angle is thus displayed.

Note that the system control circuitry 61 controls the first display 31 via the gantry control circuitry 25.

(Display Control in Case in which Subject is not Located at Predetermined Standing Position 311)

FIG. 8 is a flowchart showing the procedure of operation control in a case in which the subject is not located at the predetermined standing position 311.

As shown in FIG. 8, if the first detection signal is not received from the first sensor 33 (NO in step ST31), the system control circuitry 61 determines whether CT imaging is progressing (step ST32). If CT imaging is progressing (YES in step ST32), the system control circuitry 61 controls to stop X-ray irradiation (step ST33). More specifically, the system control circuitry 61 controls the high voltage generator 37 to stop high voltage application. The system control circuitry 61 also controls the rotation driving actuator 23 to stop the operation of the gantry 11 (step ST34). The system control circuitry 61 also controls the column driving actuator 27 to stop the operation of the gantry 11 (step ST35).

If CT imaging is not progressing (NO in step ST32), the system control circuitry 61 controls the column driving actuator 27 to inhibit the operation of the gantry 11 (step ST36). The system control circuitry 61 controls the first display 31 to display a warning to notify that the subject is not located at the predetermined standing position 311 (step ST37).

Note that the system control circuitry 61 controls the first display 31 via the gantry control circuitry 25.

(Display Control in Case in which Subject is Located Outside Imaging Region 313)

Figure 9:
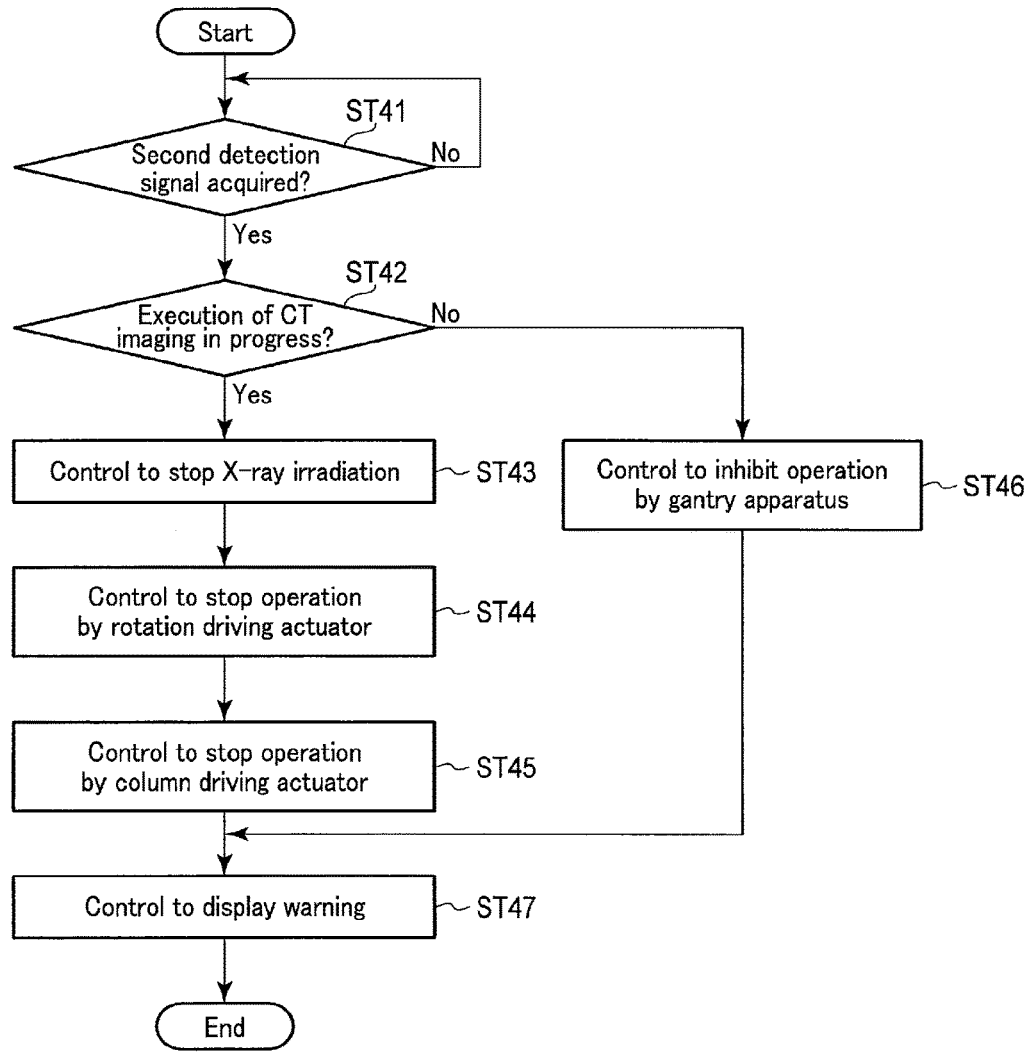
FIG. 9 is a flowchart showing the procedure of operation control in a case in which a subject is located outside the imaging region in the X-ray computed tomography imaging apparatus according to the embodiment.

FIG. 9 is a flowchart showing the procedure of operation control in a case in which the subject is located outside the imaging region 313.

As shown in FIG. 9, upon receiving the second detection signal from the second sensor 35 (YES in step ST41), the system control circuitry 61 determines whether CT imaging is progressing (step ST42). If CT imaging is progressing (YES in step ST42), the system control circuitry 61 controls to stop X-ray irradiation (step ST43). More specifically, the system control circuitry 61 controls the high voltage generator 37 to stop high voltage application. The system control circuitry 61 also controls the rotation driving actuator 23 to stop the operation of the gantry 11 (step ST44). The system control circuitry 61 also controls the column driving actuator 27 to stop the operation of the gantry 11 (step ST45).

If CT imaging is not progressing (NO in step ST42), the system control circuitry 61 controls the column driving actuator 27 to inhibit the operation of the gantry 11 (step ST46). The system control circuitry 61 controls the first display 31 to display a warning to notify that the subject is located outside the imaging region 313 (step ST47).

Note that the system control circuitry 61 controls the first display 31 via the gantry control circuitry 25.

According to the above-described arrangement, the following effects can be obtained.

The X-ray CT apparatus according to this embodiment includes an X-ray source generates X-rays, an X-ray detector detects the X-rays transmitted through the subject, a gantry including the X-ray source and the X-ray detector which are arranged to face each other a bore, a column maintains the center axis of the bore perpendicular to a floor surface and support the gantry movably in the vertical direction with respect to the floor surface, and a first display displays, on the floor surface, a graphic corresponding to a range in which a field of view formed by the X-ray source and the X-ray detector is projected onto the floor surface from the vertical direction of the gantry or a range in which the outer edge of the bore is projected onto the floor surface from the vertical direction of the gantry. The first display displays, on the floor surface, a graphic corresponding to projection of the imaging region to a part of the floor surface, thereby making the subject stand at an appropriate position.

Hence, the X-ray CT apparatus according to this embodiment can prevent the subject and the gantry from coming into contact when performing CT imaging in the standing or sitting state. That is, it is possible to provide an X-ray computed tomography imaging apparatus capable of ensuring safety of the subject when performing CT imaging in a standing or sitting state and the first display.

The term "predetermined processor" used in the above explanation means, for example, a dedicated or general-purpose processor, circuitry, processing circuitry, operation circuitry, arithmetic circuitry, an ASIC (Application Specific Integrated Circuit), a programmable logic device (for example, an SPLD (Simple Programmable Logic Device), a CPLD (Complex Programmable Logic Device), or an FPGA (Field Programmable Gate Array), or the like. Each constituent element (each processing circuitry) of the embodiment may be implemented not by a single processor but by a plurality of processors. In addition, a plurality of constituent elements (a plurality of processing circuitry) may be implemented by a single processor.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X ray computed tomography imaging apparatus, comprising:
   an X ray source configured to generate X rays;
   an X ray detector configured to detect the X rays transmitted through a subject;
   a gantry configured to hold the X ray source and the X ray detector;
   a column configured to maintain a center axis of a bore of the gantry perpendicular to a floor surface and support the gantry movably in a vertical direction with respect to the floor surface; and
   a display configured to display, on the floor surface, a graphic corresponding to one of a range in which a field of view formed by the X ray source and the X ray detector is projected onto the floor surface from the vertical direction of the gantry and a range in which an outer edge of the bore included the field of view is projected onto the floor surface from the vertical direction of the gantry, wherein the display displays one of a predetermined standing position and a predetermined sitting position of the subject in the field of view,
   wherein the apparatus further comprises
      a first sensor provided at one of the predetermined standing position and the predetermined sitting position and configured to detect whether the subject is located at one of the predetermined standing position and the predetermined sitting position; and
      a second sensor provided in the field of view and configured to detect whether the subject is located in the field of view.

2. The apparatus according to claim 1, wherein the display changes the display concerning one of the predetermined standing position and the predetermined sitting position of the subject in the field of view in accordance with examination information concerning CT imaging.

3. The apparatus according to claim 1, further comprising storage circuitry configured to store a plurality of graphics concerning the field of view,
   wherein the display comprises an input button corresponding to each of the plurality of graphics and configured to change the displayed graphic, and
   when the input button is pressed, the display displays the graphic stored in the storage circuitry and corresponding to each input button.

4. The apparatus according to claim 1, wherein the display displays additional information added to the subject in the CT imaging.

5. The apparatus according to claim 1, wherein the first sensor comprises a touch sensor configured to detect contact of the subject.

6. The apparatus according to claim 5, wherein the first sensor comprises a load sensor configured to detect a load of the subject.

7. The apparatus according to claim 5, wherein the second sensor comprises a laser sensor configured to detect the subject when the subject blocks an emitted laser beam.

8. The apparatus according to claim 1, further comprising determination circuitry configured to determine, based on a detection result of the first sensor, whether the subject is located at one of the predetermined standing position and the predetermined sitting position, and determine, based on a detection result of the second sensor, whether the subject is located outside the field of view.

9. The apparatus according to claim 8, further comprising control circuitry configured to, when it is determined that the subject is not located at one of the predetermined standing position and the predetermined sitting position, control to execute at least one of warning to the subject, inhibition of a sliding operation of the gantry, and stop of the sliding operation of the gantry, and when it is determined that the subject is located outside the field of view, control to execute at least one of warning to the subject, inhibition of the sliding operation of the gantry, and stop of the sliding operation of the gantry.

10. The apparatus according to claim 9, wherein the display displays the warning.

11. The apparatus according to claim 1, wherein the column supports the gantry rotatably about a horizontal axis, and
the display changes the displayed graphic in accordance with a rotation angle of the gantry about the rotation axis.

12. The apparatus according to claim 1, wherein the column supports the gantry movably in the vertical direction with respect to the floor surface in a state in which the center axis of the bore has a predetermined angle with respect to the floor surface, and
in the state, the display displays, on the floor surface, a graphic representing one of the range in which the field of view is projected onto the floor surface and the range in which the outer edge of the bore is projected onto the floor surface.

13. The apparatus according to claim 12, wherein the column comprises:
a slide actuator configured to support the gantry slidably in the vertical direction; and
a tilt actuator configured to support the gantry rotatably about a horizontal axis, and
the apparatus further comprises:
a first driving actuator configured to generate power to slide the gantry by the slide actuator;
a second driving actuator configured to generate power to rotate the gantry by the tilt mechanism; and
control circuitry configured to control the first driving actuator and the second driving actuator.

14. The apparatus according to claim 13, further comprising:
storage circuitry to store a plurality of graphics corresponding to a plurality of rotation angles of the gantry about the horizontal axis; and
input circuitry configured to input the rotation angle,
wherein the display displays a graphic according to the input rotation angle out of the plurality of graphics.

15. The apparatus according to claim 13, further comprising:
storage circuitry to store a graphic corresponding to a rotation angle of the gantry about the horizontal axis;
input circuitry configured to input the rotation angle; and
calculation circuitry configured to calculate a deformation amount used to deform the graphic in accordance with the input rotation angle,
wherein the display displays the graphic deformed by the calculated deformation amount.

16. A display apparatus that is used in an X ray computed tomography imaging apparatus including an X ray source configured to generate X rays, an X ray detector configured to detect the X rays, a gantry including a bore that forms an imaging region and including the X ray source and the X ray detector, a column configured to maintain a center axis of a bore of the gantry perpendicular to a floor surface and support the gantry movably in a vertical direction with respect to the floor surface, a first sensor provided at one of a predetermined standing position and a predetermined sitting position and configured to detect whether the subject is located at one of the predetermined standing position and the predetermined sitting position, and a second sensor provided in the field of view and configured to detect whether the subject is located in the field of view,
wherein the display apparatus displays, on the floor surface, a graphic corresponding to one of a range in which the field of view formed by the X ray source and the X ray detector is projected onto the floor surface from the vertical direction of the gantry and a range in which an outer edge of the bore included the field of view is projected onto the floor surface from the vertical direction of the gantry, wherein the display displays one of the predetermined standing position and the predetermined sitting position of the subject in the field of view.

* * * * *